US012496051B2

(12) United States Patent
Menand et al.

(10) Patent No.: US 12,496,051 B2
(45) Date of Patent: Dec. 16, 2025

(54) DEVICE FOR APPLYING ADHESIVE COMPOSITION TO BIOLOGICAL TISSUE AND/OR PROSTHETIC MATERIAL

(71) Applicant: Tissium, Paris (FR)

(72) Inventors: Simon Menand, Paris (FR); Estelle Collin, Alfortville (FR); Louise Vaguelsy, Paris (FR); Christophe Naz, Fontainebleau (FR)

(73) Assignee: Tissium (FR)

( * ) Notice: Subject to any disclaimer, the term of this patent is extended or adjusted under 35 U.S.C. 154(b) by 382 days.

(21) Appl. No.: 18/024,638

(22) PCT Filed: Mar. 26, 2021

(86) PCT No.: PCT/EP2021/058034
§ 371 (c)(1),
(2) Date: Mar. 3, 2023

(87) PCT Pub. No.: WO2022/048799
PCT Pub. Date: Mar. 10, 2022

(65) Prior Publication Data

US 2024/0023947 A1 Jan. 25, 2024

(30) Foreign Application Priority Data

Sep. 3, 2020 (EP) .................................... 20305979

(51) Int. Cl.
*A61B 17/00* (2006.01)

(52) U.S. Cl.
CPC .. *A61B 17/00491* (2013.01); *A61B 2017/005* (2013.01)

(58) Field of Classification Search
CPC .............. A61B 17/00491; A61B 17/11; A61B 17/1114; A61B 17/1128;
(Continued)

(56) References Cited

U.S. PATENT DOCUMENTS

2007/0250114 A1* 10/2007 Drapeau ............ A61B 17/1146 606/152
2010/0211172 A1 8/2010 Bellamkonda et al.
(Continued)

FOREIGN PATENT DOCUMENTS

EP 2073724 A2 7/2009
WO 2008029373 A3 5/2008

OTHER PUBLICATIONS

Extended European Search Report including Written Opinion for Application No. 20305979.5 dated Mar. 1, 2021, pp. 1-9.
(Continued)

*Primary Examiner* — Todd J Scherbel
(74) *Attorney, Agent, or Firm* — Lerner David LLP

(57) ABSTRACT

A device for applying adhesive composition to biological tissue and/or prosthetic material includes a flexible body, wherein the body has an upper surface that includes a first shoulder defining a first recess. The body is adapted to be folded on itself in a folded position in which the body defines a channel and in which the first recess forms an annular gap between the upper surface and the biological tissue and/or prosthetic material when the biological tissue and/or prosthetic material is positioned in the channel.

18 Claims, 14 Drawing Sheets

(58) Field of Classification Search
CPC .... A61B 2017/00495; A61B 2017/005; A61B 2017/00504; A61B 2017/00508; A61B 2017/00513; A61B 2017/00517; A61B 2017/00522; A61B 2017/1107; A61B 2017/1132
See application file for complete search history.

(56) References Cited

U.S. PATENT DOCUMENTS

| | | | |
|---|---|---|---|
| 2012/0078293 | A1 | 3/2012 | Hassidov et al. |
| 2013/0261542 | A1* | 10/2013 | Elachchabi ........... A61F 2/0063 604/93.01 |
| 2014/0024885 | A1 | 1/2014 | Sudekum |
| 2015/0359605 | A1 | 12/2015 | O'Brien-Coon et al. |
| 2022/0226543 | A1* | 7/2022 | Yaszemski .......... A61L 27/3834 |

OTHER PUBLICATIONS

International Search Report for Application No. PCT/EP2021/058034 mailed Apr. 20, 2021, pp. 1-4.

* cited by examiner

DEVICE FOR APPLYING ADHESIVE COMPOSITION TO BIOLOGICAL TISSUE AND/OR PROSTHETIC MATERIAL

CROSS-REFERENCE TO RELATED APPLICATIONS

The present application is a national phase entry under 35 U.S.C § 371 of International Application No. PCT/EP2021/058034 filed Mar. 26, 2021, which claims priority from European Application No. 20305979.5 filed Sep. 3, 2020, all of which are hereby incorporated herein by reference.

TECHNICAL FIELD

The present disclosure deals with a device for applying adhesive composition to biological tissue and/or prosthetic material. According to a specific embodiment, the device of the invention can be used in nerve surgery and vascular surgery.

BACKGROUND

Anastomosis is a surgical technique in which two separate tubular biological structures of a mammal, such as nerve stumps or blood vessels, are joined to form a functional element. Suture is the gold standard for anastomosis. However, suturing is generally difficult to perform and requires great skill and experience of the surgeon. Suturing is also susceptible to complications resulting from damage to the tissues, leakage, stimulation of an inflammatory response and potential infection around the suture material.

Adhesive compositions have been proposed as an alternative to suture (see for instance “Tissue engineering and peripheral nerve reconstruction: an overview”, by Geuna et al., 2013) but they have proved not easy to implement. For example, it has been proposed to apply cyanoacrylate directly onto the nerve stumps, nevertheless nerve is very soft, making it difficult to maintain the correct position of the nerve ends when gluing them. To improve suture-less anastomosis, it has been proposed to use tubular prosthetic structures commonly referred to as neural guides or “neuroguides” which contributes to better fixing of the nerve ends and to avoiding the invasion of glue into the nerve ends. However, the procedures with these conduits become a little more complicated, reducing the time savings, which is an important feature of the adhesive composition method. Moreover, application of the adhesive composition still suffers from incorrect glue distribution with accidental flow of part of the adhesive in front of the nerve stump bringing the misfortunate consequence of sealing it and impairing the regeneration process.

SUMMARY OF THE INVENTION

The present invention relates to a device which facilitates application of adhesive composition to biological tissue and/or prosthetic material, improves distribution of the adhesive composition and facilitates suture-less microsurgery.

A first aspect of the invention is a device for applying adhesive composition to biological tissue and/or prosthetic material, the device comprising a flexible body, wherein:

- the body has an upper surface comprising a first shoulder defining a first recess and two longitudinal edges,
- the body is adapted to be folded on itself in a folded position in which the body defines a channel and said first recess is configured to form an annular gap between the upper surface and the biological tissue and/or prosthetic material when the biological tissue and/or prosthetic material is positioned in the channel, and
- the first recess extends along a first longitudinal edge of the body.

According to the invention, “biological tissue, prosthetic material or combination thereof” are further referred to “tubular structure”. According to the invention, “biological tissue” can be tubular biological structure such as for example nerve, blood vessel, tendon, ligament and the like. According to the invention, “prosthetic material” can be a scaffold for tissue repair or regeneration, e.g. a tube or conduit, for example a guide conduit such as conduits for helping to connect blood vessel, nerve guide for nerve regeneration or tendon and ligament repair device.

The device according to the first aspect may comprise the following features, taken separately or in combination whenever it is technically feasible.

The first recess may have a depth from about 0.1 millimeters to about 10 millimeters.

The body may further comprise a curved protrusion defining a concave portion of the upper surface.

The curved protrusion may have a wave-shaped profile.

The first shoulder may extend in the curved protrusion.

The curved protrusion may have a radius of curvature from about 1 millimeter to about 15 millimeters, more particularly from about 1 millimeter to about 10 millimeters, and even more particularly from about 1 millimeter to about 5 millimeters.

The curved protrusion may extend over an angular sector of at least 90 degrees, preferably at least 180 degrees.

The device may comprise a deformable flap defining a deformable portion of the body and further defining a first end of the body, wherein the channel is defined by the curved protrusion and the deformable flap.

The device may further comprise a prehensile flap defining a second end of the body which is opposite to the first end, and wherein the curved protrusion connects the prehensile flap to the deformable flap.

The upper surface of the body may comprises a second shoulder defining a second recess spaced from the first recess, wherein the second recess extends along the second longitudinal edge of the body and the body may be adapted to be folded on itself into a folded position in which the body defines a channel and said first recess is configured to form a first annular gap and said second recess is configured to form a second annular gap, both annular gaps being formed between the upper surface of the body and the biological tissue and/or prosthetic material when the biological tissue and/or prosthetic material is positioned in the channel.

The body may comprise a rib separating the second recess from the first recess, said first and second shoulders extending along respective lengthwise edges of the rib.

The rib may have a width, measured as a distance between the first recess and the second recess, which is from about 1 millimeter to about 10 millimeters.

The first recess and/or the second recess may have a width measured, respectively, as a distance between the first recess and the first longitudinal edge of the body and/or between the second recess and the second longitudinal edge of the body, from about 1 millimeter to about 10 millimeters.

The body may have a rectangular shape.

The device may further comprise means for maintaining the body in the folded position, such as at least one magnet and at least one metallic element cooperating with the magnet.

The upper surface may have an average surface roughness below 1 Ra, preferably below 0.5 Ra.

The body may be translucent.

The flexible material of the body may contain silicone.

A second aspect of the invention is a kit comprising a device according to the first aspect of the invention, and an adhesive composition, more particularly an adhesive composition able to polymerize when exposed to light.

This kit may further comprise prosthetic material and preferably a scaffold for tissue regeneration, such as for example nerve guide (e.g. nerve conduit or nerve wrap) for nerve regeneration or tendon repair device. Examples of nerve guide such as nerve conduit or nerve wrap are, respectively, Neuroflex™ or Neuromead™ from NerveRepair. Example of tendon repair device is disclosed in US2014/0024885.

A third aspect of the invention is a use of the device according to the first aspect or the kit according to the second aspect for connecting/anastomosing tubular structures.

A fourth aspect of the invention is a method for anastomosing two tubular biological structures of a mammal, the method comprising:

- arranging respective ends of both tubular biological structures in a tubular prosthetic material such that both ends face each other in the tubular prosthetic material hereby forming tubular scaffold,
- positioning the unfolded flexible body of the device of the Invention under the tubular scaffold,
- applying an adhesive composition around the tubular prosthetic material and around at least one of the tubular biological structures so as to form a junction between said tubular biological structure and the tubular prosthetic material,
- folding the flexible body, such that the tubular scaffold extends in the channel defined by the body, and such that the annular gap formed by the first recess extends between the tubular scaffold and the upper surface of the body.

According to the Invention, the adhesive composition may be an adhesive composition able to polymerize when exposed to light and the method may further comprise exposing the layer of adhesive composition to light so as to induce polymerization of the adhesive composition.

DESCRIPTION OF THE DRAWINGS

Further details, features and advantages of the invention are explained in more detail below with the aid of the exemplary embodiments of the invention that are illustrated in the figures in which.

Similar features have same reference numerals in all figures.

DETAILED DESCRIPTION OF THE INVENTION

Figure 1:
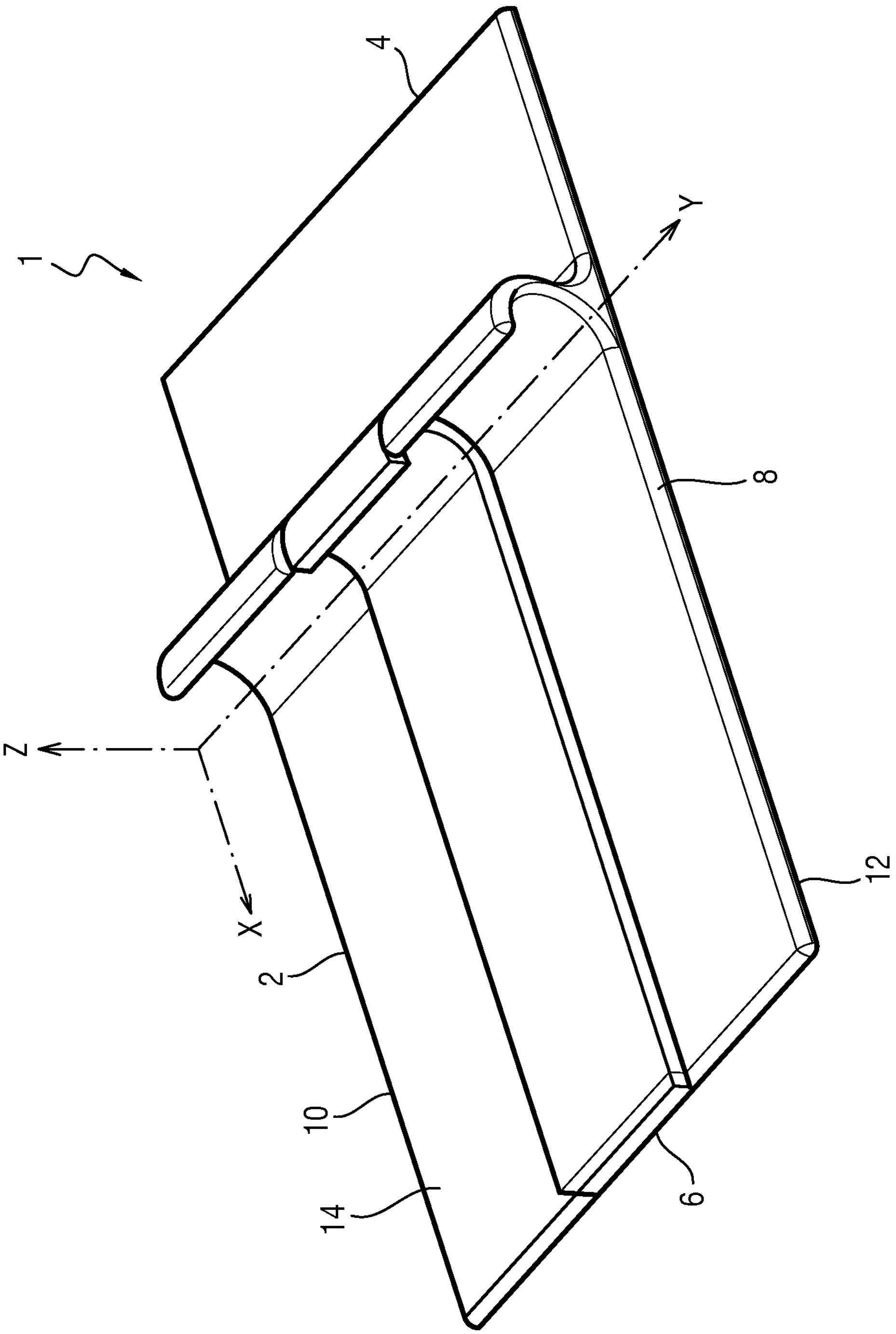
FIG. 1 is a perspective view of a device according to a first embodiment in an unfolded position.

Is shown in FIG. 1 a device according to a first embodiment, which is a preferred embodiment. Device 1 according to a preferred embodiment comprises a body 2. Body 2 is flexible. Due to its flexibility, the body 2 is able to be positioned in many positions, including an unfolded position as shown in FIG. 1. According to the present invention, “flexible” or “flexibility” have the meaning given in the art, i.e. capable of bending without breaking.

Body 2 extends in three directions: a longitudinal direction indicated by axis X, a transversal direction indicated by axis Y, and a third (vertical) direction indicated by axis Z. Axes X, Y and Z are orthogonal. In the present disclosure, lengths, widths and heights of parts of the device will be discussed. By convention, lengths are measured in the longitudinal direction, widths are measured in the transversal direction, and heights are measured in the third (vertical) direction.

Body 2 has a first transversal edge 4 and a second transversal edge 6 opposite to first transversal edge 4. Body 2 extends in the longitudinal direction from first transversal edge 4 to second transversal edge 6. Transversal edges 4, 6 are parallel.

Body 2 has a length comprised from about 10 millimeters to about 50 millimeters, preferably from about 20 millimeters to about 40 millimeters, more preferably from about 30 millimeters to about 40 millimeters.

The term “about” as used herein means within 20%, preferably within 10%, and more preferably within 5%. In specific case, “about X”, means “X”.

Body 2 has a first longitudinal edge 8 and a second longitudinal edge 10 opposite to first longitudinal edge 8. Body 2 extends in the transversal direction from the first longitudinal edge 8 to the second longitudinal edge 10. Longitudinal edges 8, 10 are parallel.

Body 2 has a width smaller than its length.

The width of body 2 is comprised from about 5 to about 30 millimeters, preferably from about 10 millimeters to about 20 millimeters, more preferably from about 12.5 to about 20 millimeters, for instance it is 16 millimeters.

Body 2 further has a lower surface 12 and an upper surface 14 opposite to the lower surface 12. Body 2 extends in the vertical direction from lower surface 12 to upper surface 14. Lower surface 12 and upper surface 14 are joined together by transversal edges 6, 4 and longitudinal edges 8, 10.

Figure 4:
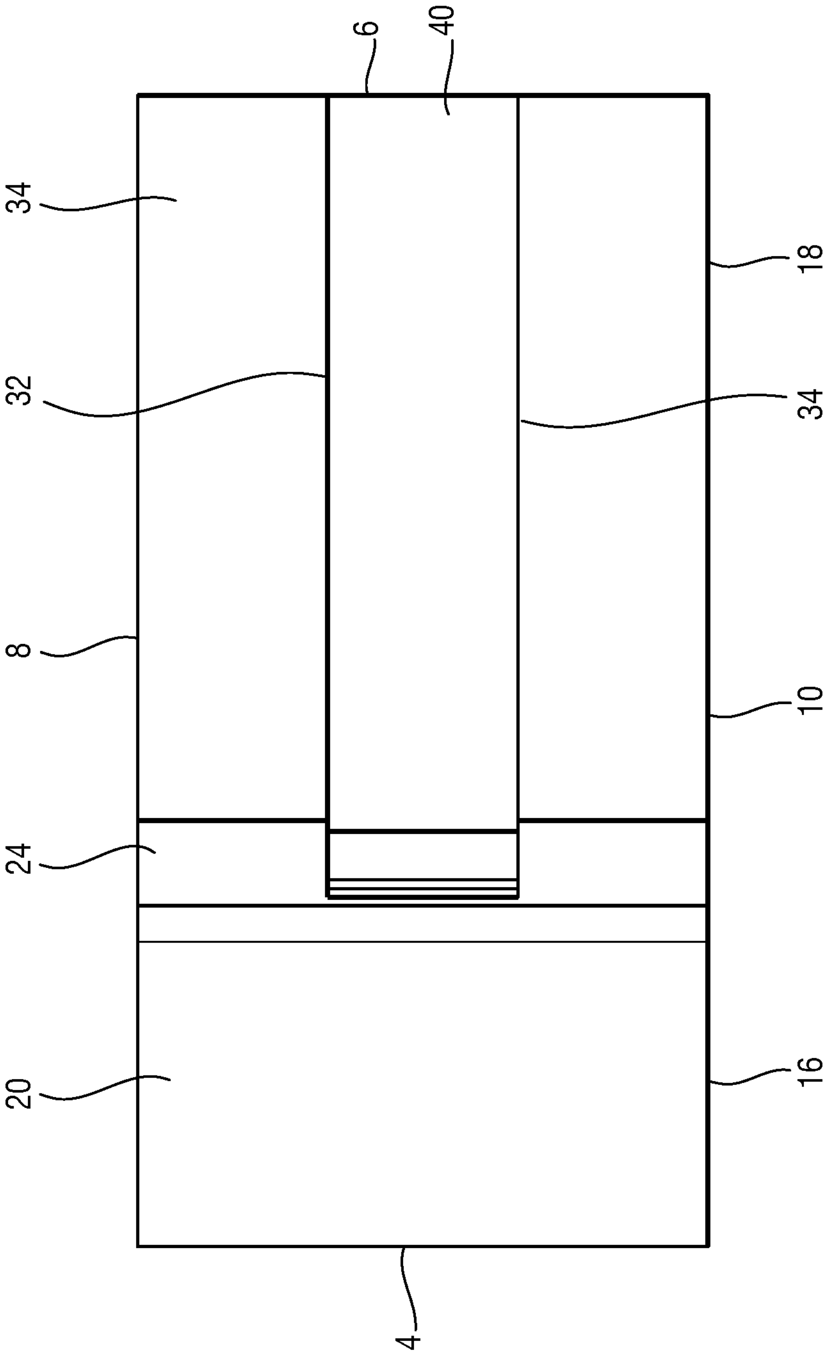
FIG. 4 is a top view of the device of FIGS. 1-3.

Lower surface 12 is planar. Body 2 may have a rectangular shape, in the sense that the lower surface is rectangular (as shown in FIG. 4).

Upper surface 14 is non-planar. As a consequence, the height of body 2 is not constant. The shape of said upper surface 14 is further detailed hereinafter.

Figure 2:
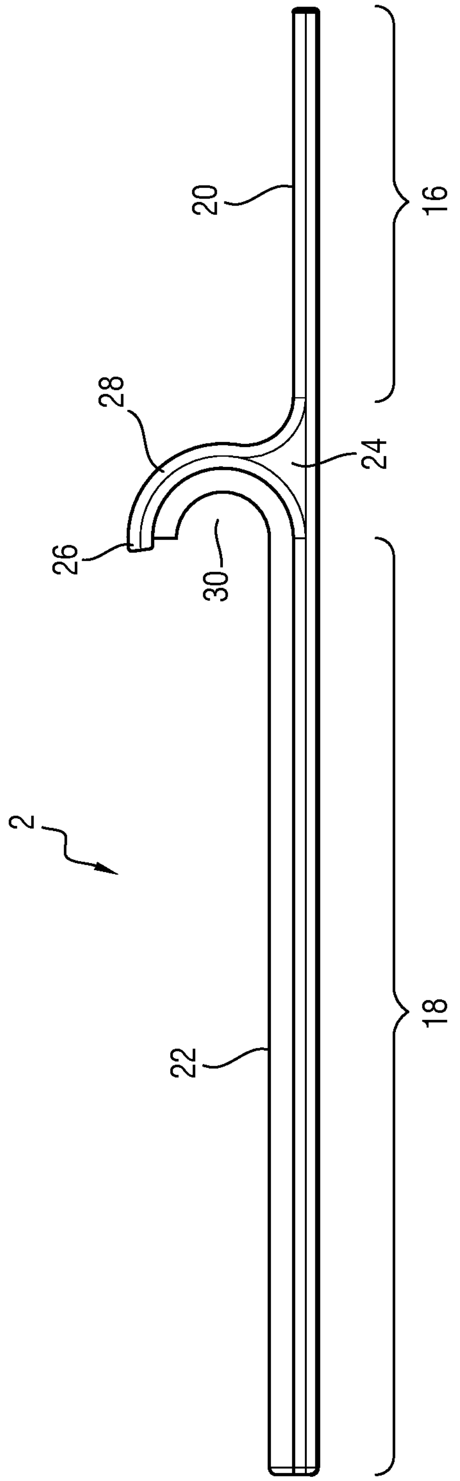
FIG. 2 is a side view of the device depicted in FIG. 1.

In the preferred embodiment, body 2 comprises a first flap 16 and a second flap 18 (FIG. 2).

First flap 16 defines the first transversal edge 4 of body 2. First flap 16 is substantially flat.

First flap 16 has an upper surface 20, which is referred to as first upper surface 20 hereinafter. First upper surface 20 is a first portion of overall upper surface 14 of body 2. Upper surface 20 may be planar.

Second flap 18 defines the second transversal edge 6 of body 2.

Second flap 18 has an upper surface 22, which is referred to as second upper surface 22 hereinafter. Second upper surface 22 is a second portion of overall upper surface 14 of body 2. Second upper surface 22 is non planar.

Second flap 18 may have a length which is greater than that of first flap 16. Preferably, the length of second flap 18 is at least twice the length of first flap 16.

The length of second flap 18 is from about 10 millimeters to about 30 millimeters, preferably from about 20 to about 30 millimeters.

Second flap 18 may have a height which varies along axis Y from about 0.25 millimeters to about 3 millimeters, preferably from about 0.3 millimeters to about 1.5 millimeters, for instance it is about 0.8 millimeter at its maximum height (i.e. top of the first shoulder 32) and about 0.3 millimeters at its minimum height (i.e. bottom of the first recess).

In the preferred embodiment, body 2 further comprises a curved protrusion 24 which protrudes in the vertical direction with respect to the first and second flap 18.

Curved protrusion 24 connects first flap 16 to second flap 18. When body 2 is in its unfolded position, curved protrusion 24 is located between flaps 16 and 18.

Curved protrusion 24 has a top 26, an outer side 28 and in inner side 30 opposite to outer side 28.

The maximum height of body 2, measured between lower surface 12 and top 26, is lower than about 8 millimeters, preferably lower than about 7 millimeters, for instance it is about 7 millimeters or about 4 millimeters.

Top 26 of curved protrusion 24 defines a groove 27.

Curved protrusion 24 has the shape of a wave. The wave is hemmed and directed towards the second transversal edge 6 of body 2. Outer side 28 actually forms a back of the wave, and inner side 30 forms a front of the wave.

Outer side 28 is a curved surface extending first upper surface 20 defined by first flap 16, for instance continuously. A majority of outer side 28 is convex.

Inner side 30 of curved protrusion 24 is a concave surface defining an open cavity extending along axis Y. This cavity is intended to receive biological tissue and/or prosthetic material.

Concave surface 30 continuously extends second upper surface 22 defined by second flap 18.

Concave surface 30 has a concave cross-section in a transversal plane perpendicular to the transversal direction.

Concave surface 30 has a radius of curvature from about 1 millimeter to about 15 millimeters, more particularly from about 1 millimeter to about 10 millimeters, and even more particularly from about 1 millimeter to about 5 millimeters.

Concave surface 30 extends over an angular sector around axis Y. Said angular section is greater than 90 degrees, for instance 180 degrees (FIG. 2).

Figure 3:
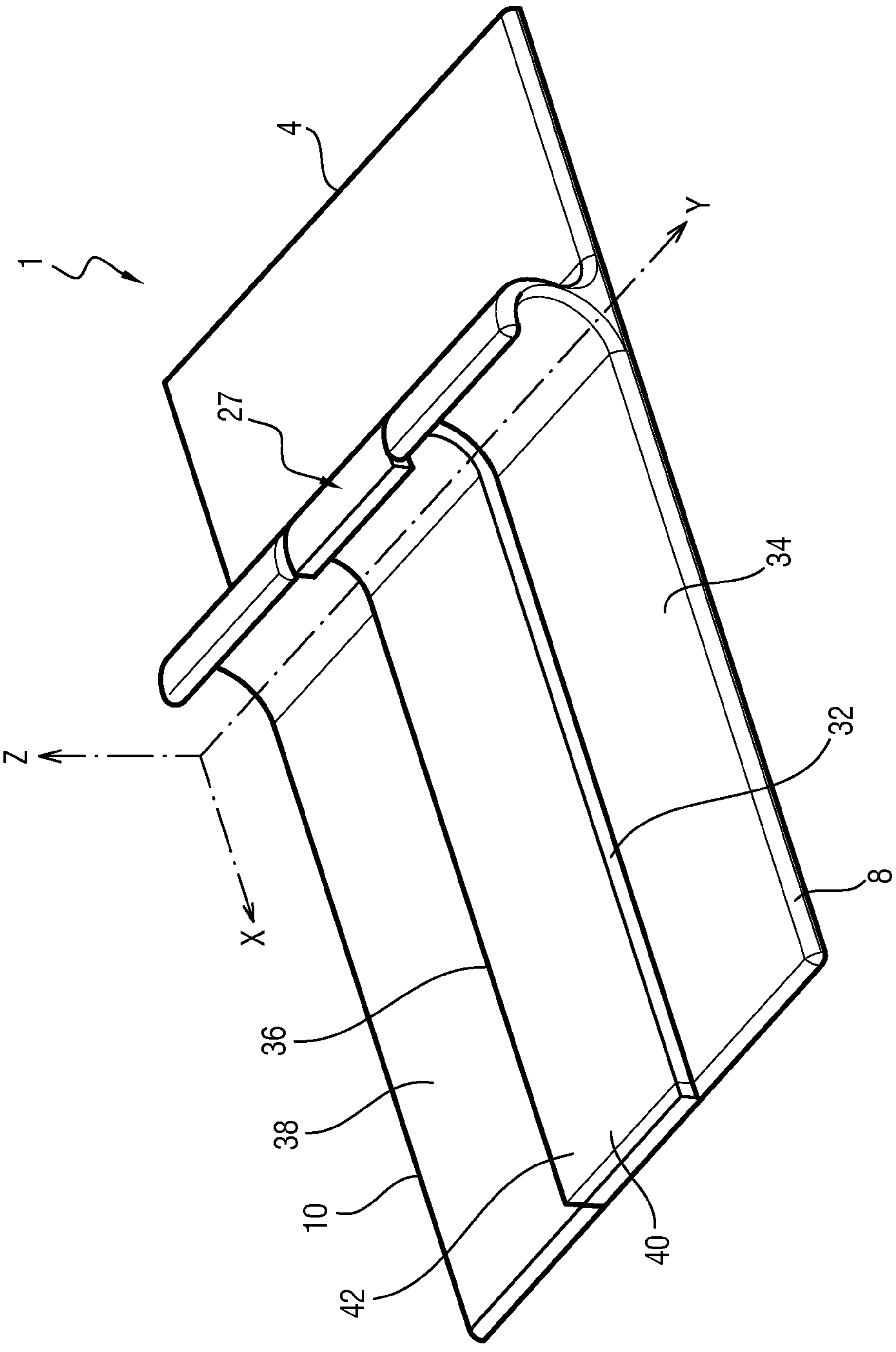
FIG. 3 is another perspective view of the device of FIGS. 1-2.

According to the invention, the upper surface 14 of body 2 comprises a first shoulder 32 defining a first recess and at least one first recessed surface 34 forming a bottom of the said first recess (as shown in FIGS. 3-4). The first recess extends along the first longitudinal edge 8.

In the preferred embodiment comprising curved protrusion 24, the first shoulder 32, the first recess and the first recessed surface 34 extend in second upper 22 (defined by second flap 18) and further extend in curved surface 30 (defined by curved protrusion 24).

First recessed surface 34 may extend in the transversal direction from first longitudinal edge 8 to first shoulder 32.

Besides, the first recess has a width from about 1 millimeter to about 10 millimeters. For example, the width of the first recess is 5+/−0.15 millimeters.

According to another embodiment, the invention relates to a device 1 as defined above wherein upper surface 14 of body 2 further comprises a second shoulder 36 defining a second recess, and comprises a second recessed surface 38 forming a bottom of the second recess.

The second recess extends along the second longitudinal edge 10. The second recess is distant from the first recess.

In the preferred embodiment comprising curved protrusion 24, the second shoulder 36, second recess and second recessed surface 38 extend in second upper surface 22 (defined by second flap 18) and further extend in curved surface 30 (defined by curved protrusion 24) (FIGS. 1,3 and 4).

Second recessed surface 38 may extend in the transversal direction from second longitudinal edge 10 to second shoulder 36.

Besides, the second recess has a width from about 1 millimeter to about 10 millimeters. For example, the width of the second recess is 5+/−0.15 millimeters.

According to the invention, body 2 comprises a rib 40 along first recess.

When the device 1 of the invention is comprising a first shoulder 32 and a second shoulder 36 said rib 40 is separating the first recess from the second recess. In other words, rib 40 separates first recessed surface 34 from second recessed surface 38.

Rib 40 protrudes in upper surface 14. Rib 40 has a top 42 which is elevated with respect to first recessed surface 34 and second recessed surface 36.

First shoulder 32 forms a first longitudinal rib edge of rib 40 joining top 40 and first recessed surface 34. The first longitudinal rib edge is a surface perpendicular to the transversal direction.

Second shoulder 36 is opposite to the first shoulder 32 relative to rib 40. Second shoulder 36 forms a second longitudinal rib edge of rib 40 joining top 42 and second recessed surface 38. The second longitudinal rib edge is a surface perpendicular to the transversal direction.

Rib 40 may have a width, measured as a distance between the first recess and the second recess (i.e. from first shoulder 32 to second shoulder 36 in the transversal direction), which is substantially equal to that of groove 27 when present.

The width of rib 40 is from about 1 millimeter to about 10 millimeters, preferably from about 2.5 millimeters to about 7.5 millimeters.

Figure 5:
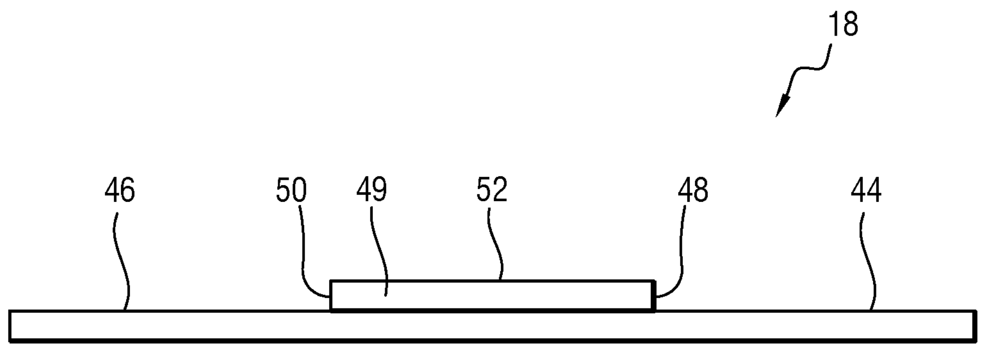
FIG. 5 shows a cross-section of the device of FIGS. 1-4.

FIG. 5 shows a cross-section of second flap 18 in a plane perpendicular to the longitudinal direction, second flap 18 defines a planar surface portion 44 of first recessed surface 34 and a planar surface portion 46 of the second recessed surface 38. Said planar surface portions 44 and 46 may be coplanar.

First shoulder 32 comprises a linear shoulder portion 48 and second shoulder 34 comprises a linear shoulder portion 50.

Rib 40 comprises a linear rib portion 49 extending in the second flap 18. When the device 1 of the invention is comprising a first shoulder 32 and a second shoulder 36 said linear rib portion 49 separates planar surface portions 44, 46 from each other.

Linear rib portion 49 further defines a planar top 52, which is a portion of top 42. Planar top 52 is parallel to planar surface portions 44, 46.

First linear shoulder portion 48 connects planar top 52 to planar surface portion 44. Similarly, second linear shoulder portion 50 connects planar top 52 to planar surface portion 46.

The height of linear rib portion 49 is for example half the highest height of second flap 18.

Figure 6:
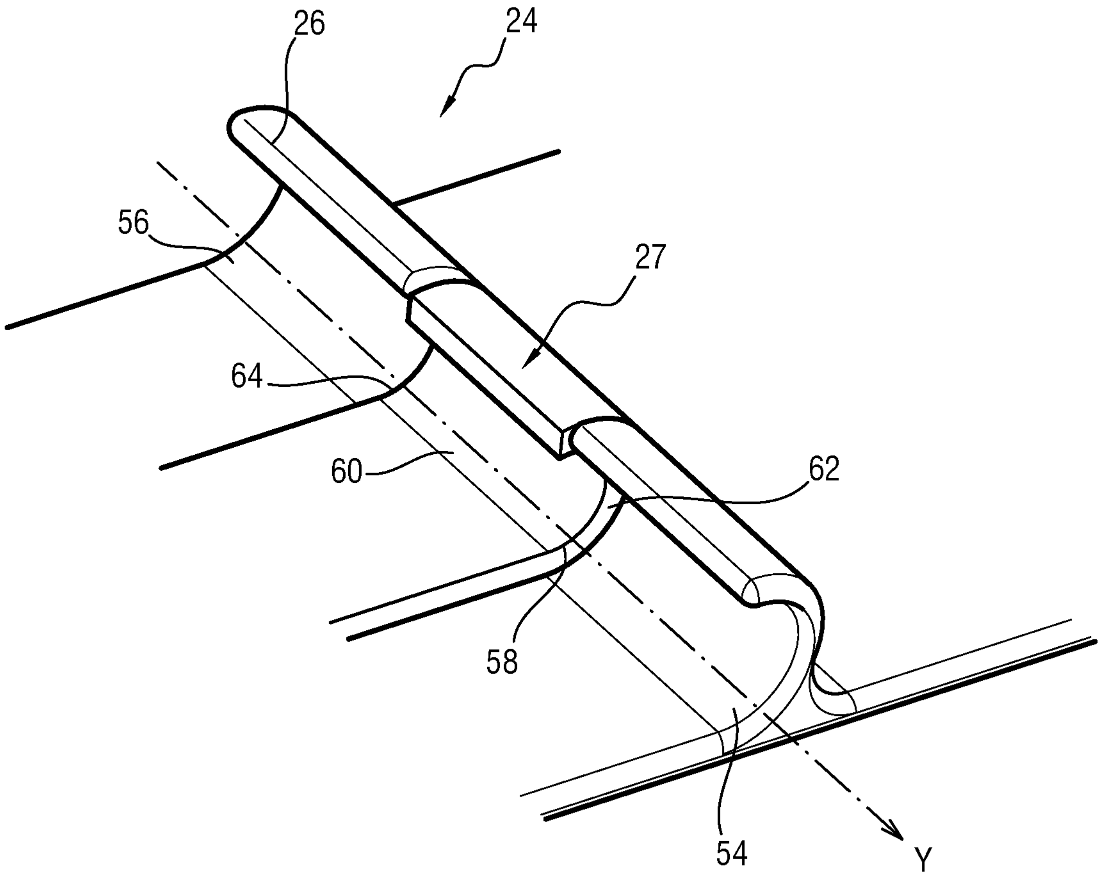
FIG. 6 is a perspective view of a curved protrusion of the device of FIGS. 1-5.

As shown in FIG. 6, curved protrusion 24, when present, defines a first concave recessed surface 54. First recess surface is a concave portion of first recessed surface 34.

Concave recessed surface 54 has a first radius of curvature.

Similarly, when the device 1 of the invention is comprising a first shoulder 32 and a second shoulder 36, curved protrusion 24 defines a second concave recessed surface 56. Second concave recessed surface is a concave portion of second recessed surface 38.

Concave recessed surface 56 has a second radius of curvature. Second radius of curvature may be equal to the first radius of curvature.

Rib 40 comprises a concave rib portion 58 extending in curved protrusion 24. Concave rib portion 58 defines a middle zone of the open cavity intended to receive biological tissue and/or prosthetic material aforementioned. Concave rib portion 58 may separate concave surface recessed surfaces 54 and 56 from each other.

Concave rib portion 58 further defines a concave top 60. Concave top 60 is a curved portion of top 42 of rib 40. Concave top 60 has a third radius of curvature smaller than the first and second radius of curvature.

The height of concave rib portion 58, measured in a radial direction towards axis Y, is equal to the height of linear rib portion 49.

First shoulder 32 comprise a first concave shoulder portion 62. First concave shoulder portion 62 connects concave top 60 to first concave recessed surface 54.

Similarly, second shoulder 34 comprises a second concave shoulder portion 64. Second concave shoulder portion 64 connects concave top 60 to second concave recessed surface 56.

Body 2 may be a single piece. Body 2 may be obtained by injection molding.

Body 2 preferably contains silicone or is made of silicone. Silicone has the following advantages: it is flexible, resilient and biocompatible.

Body 2 is transparent or translucent. Body 2 is preferably able to be crossed by radiations having a wavelength comprised between 350 and 670 nanometers, preferably of 405 nanometers.

Upper surface 14 may have an average surface roughness below 1 Ra, preferably below 0.5 Ra. Such roughness is advantageous in that it prevents objects such as tubular structure, more particularly biological tissue and/or prosthetic material, laying on upper surface 14 from slipping.

Body 2 is flexible, thus it is able to be positioned in many positions, including unfolded position as discussed above and shown in FIGS. 1-6.

Figure 7:
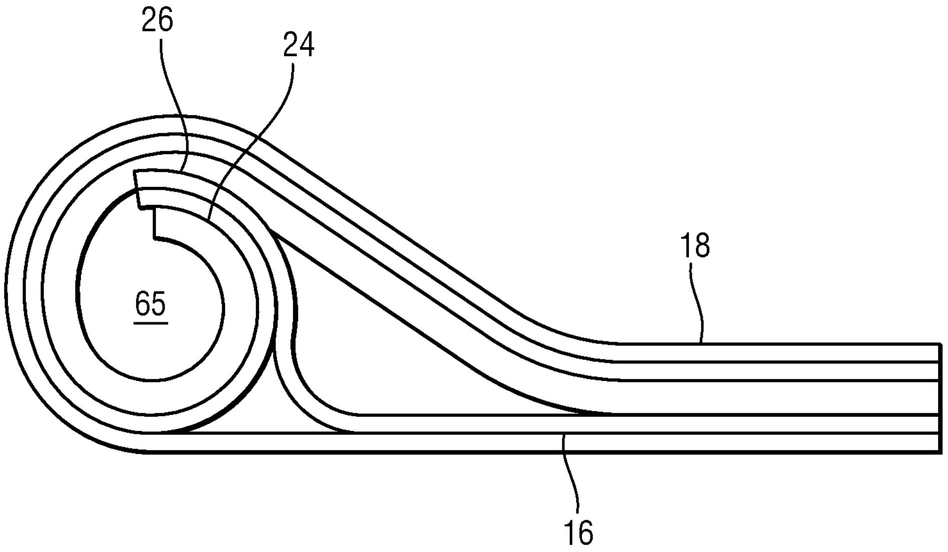
FIG. 7 is a side view of the device depicted in FIG. 1 in a folded position.

Flexible body 2 can be positioned in a folded position different from the unfolded position (as shown in FIG. 7).

The flexible body 2 can switch from unfolded position to folded position by winding second flap 18 on itself, such that second flap 18 closes the open cavity defined by curved protrusion 24. When body 2 is in folded position, second flap 18 covers curved protrusion 24 and can rest on its top 26. Rib 40 can engage groove 27, if present. This engagement is advantageous to align second flap 18 relative to curved protrusion 24.

Second flap 18 is long enough such that a terminal portion of surface 22 gets past curved protrusion 24 and faces upper surface 20 defined by first flap 16, when body 2 is in folded position.

The closed cavity defined by curved protrusion 24 and second flap 18 is a globally tubular channel 65 extending along transversal axis Y. Said channel 65 has a first opening defined by first longitudinal edge 8 and a second opening defined by second longitudinal edge 10.

In folded position, rib 40 is wound on itself as well. The first recess defined by first shoulder 32 and first recessed surface 34 forms a first annular gap extending around transversal axis Y. Similarly, when present, the second recess defined by second shoulder 36 and second recessed surface 38 forms a second annular gap extending around transversal axis Y.

A tubular structure, such as biological tissue and/or prosthetic material, can be positioned in channel 65 so as to rest on wounded rib 40 without contacting first recessed surface 34 and/or second recessed surface 38. As a consequence, both annular gaps can extend all around said tubular structure.

Device 1 may further comprise maintaining means for maintaining body 2 in folded position when needed. Having such means in device 1 allows to leave user's hands free once device 1 is folded.

The maintaining means comprise at least one first fastening element 66 and at least one second fastening element 68 adapted to cooperate with the first fastening element 66, when body 2 is in folded position.

For instance, at least one of first fastening element 66 is embedded in first flap 16, and at least one second fastening element is embedded in second flap 18.

For example, first and second fastening elements 66, 68 are a magnet and a metallic element able to be attracted to the magnet.

Figure 8:
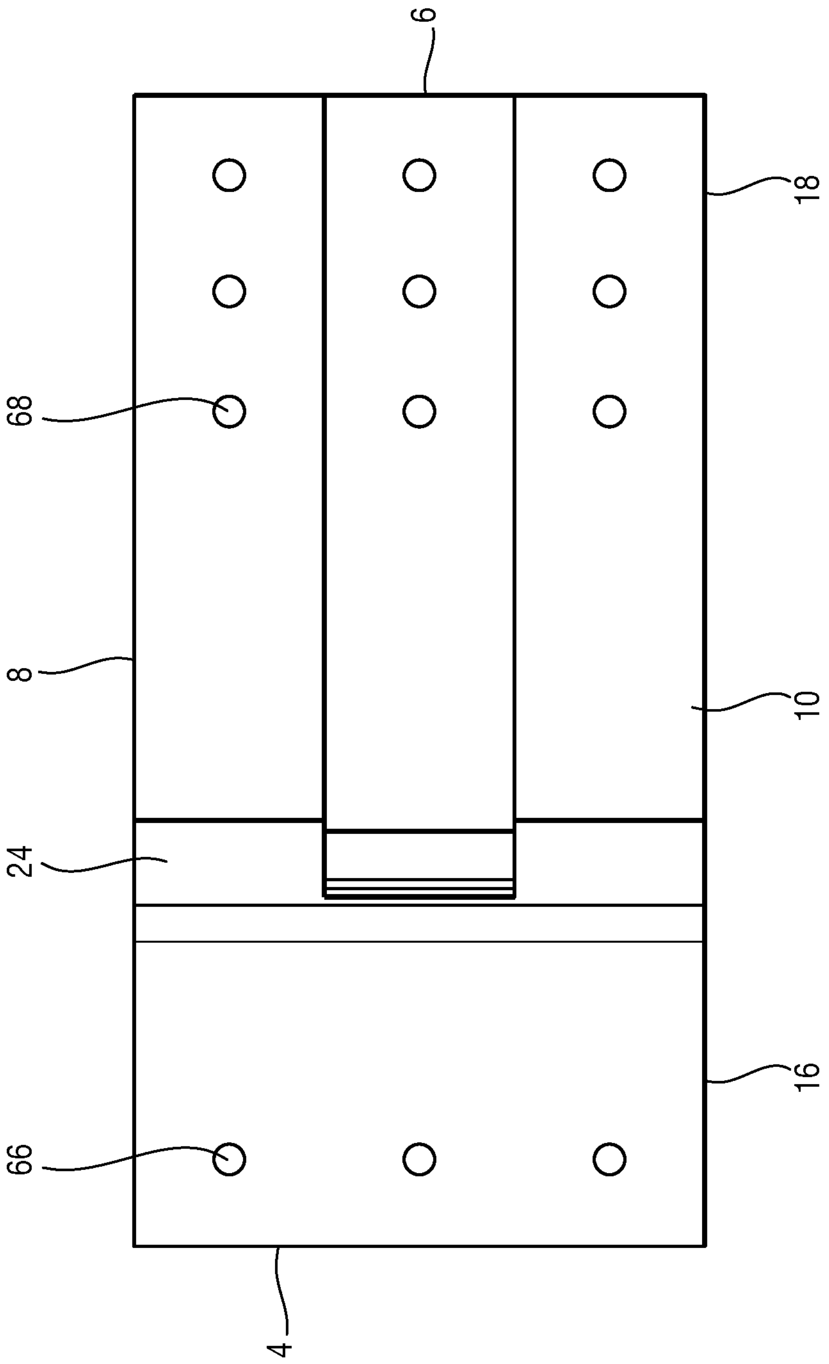
FIG. 8 is another top view of the device of FIGS. 1-7.

A row of N first fastening elements 66 may be arranged in first flap 16. Fastening elements 66 are aligned in the transversal direction. Besides, at least one row of N second fastening elements 68 is arranged in second flap 18. The fastening elements 68 of each row are aligned in the transversal direction as well. In the embodiment shown in FIG. 8, N=3 and the number of rows is three, thus the total number of second fastening elements 68 is 9. A row of second fastening elements 68 comprises: a first fastening element arranged in first recessed surface 34, a second fastening element arranged in second recessed surface 38, and a third fastening element arranged in rib 40.

According to another embodiment (not shown in the figures), the maintaining means comprise an attach which is not permanently attached to body 2. This attach comprises a least one third fastening element that can cooperate with a first fastening element 66 and a second fastening element 68. For instance, the first and second fastening element are female elements, and the third fastening element is a male adapted to engage both first and second fastening element simultaneously when the body is in its folded position.

Figure 9:
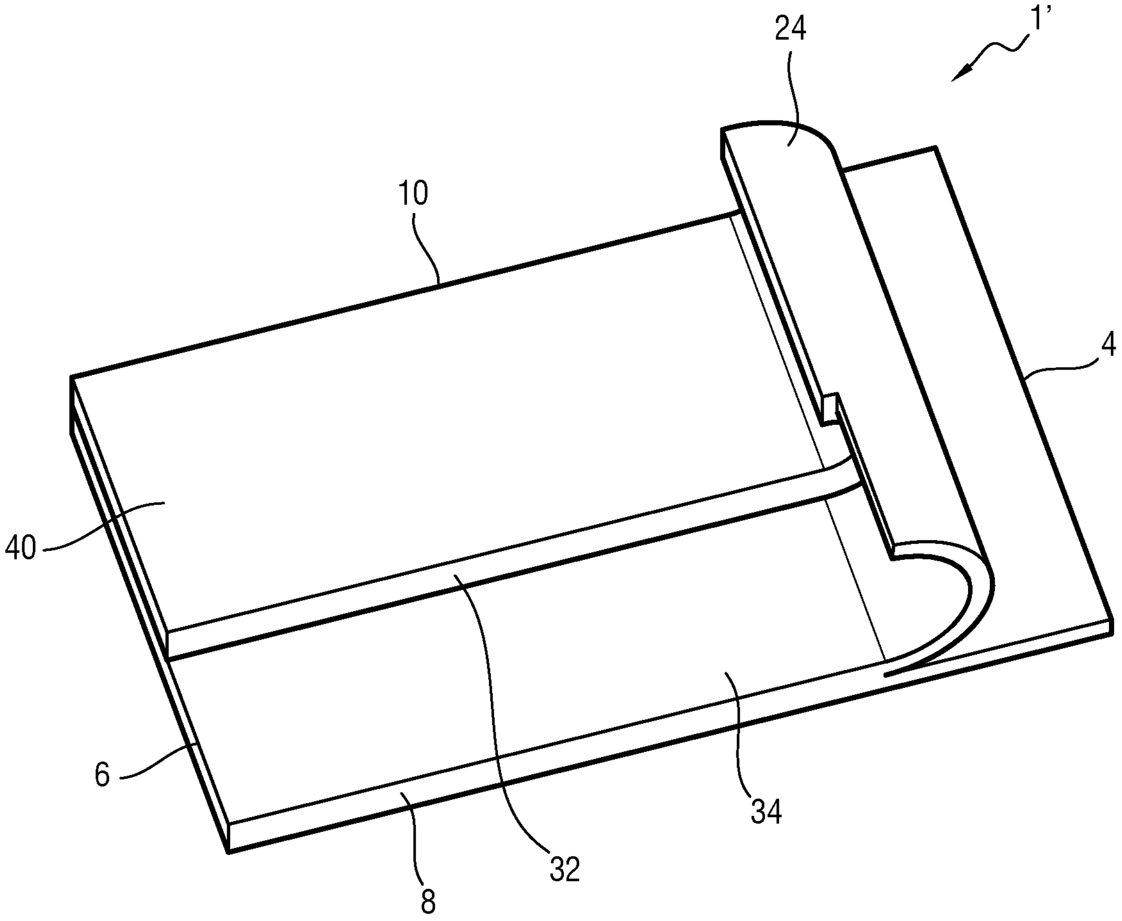
FIG. 9 is a perspective view of a device according to a second embodiment in an unfolded position.

A device 1' according to a second embodiment is shown in FIG. 9.

Device 1' mainly differs from device 1 in that it comprises one single shoulder 32. Rib 40 extends from shoulder 32 to longitudinal edge 10. All other features discussed above in relation with device 1 may be included in device 1' (including the exemplary material aforementioned for flexible body 2, as well as the maintaining means discussed in relation with FIG. 8).

Figure 10:
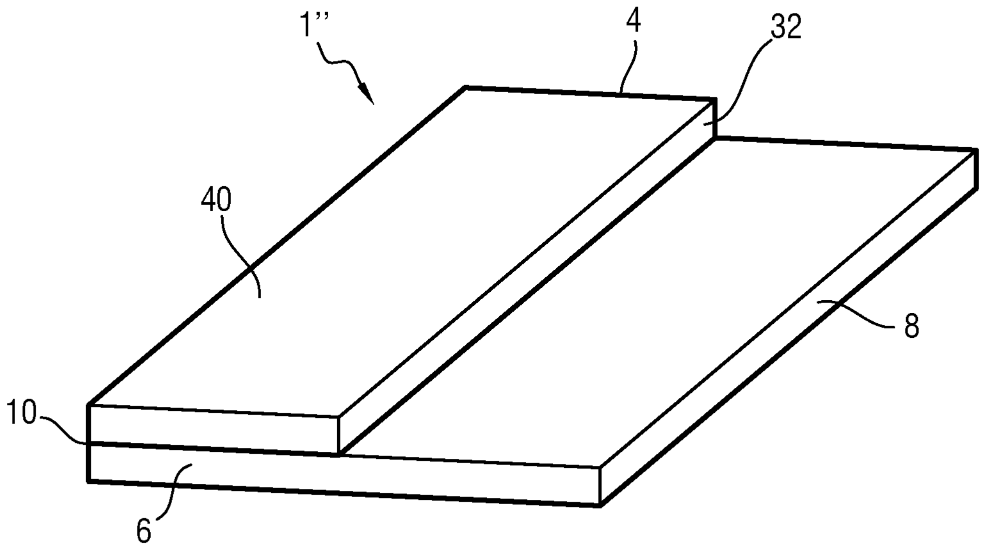
FIG. 10 is a perspective view of a device according to a third embodiment in an unfolded position.
Figure 11:
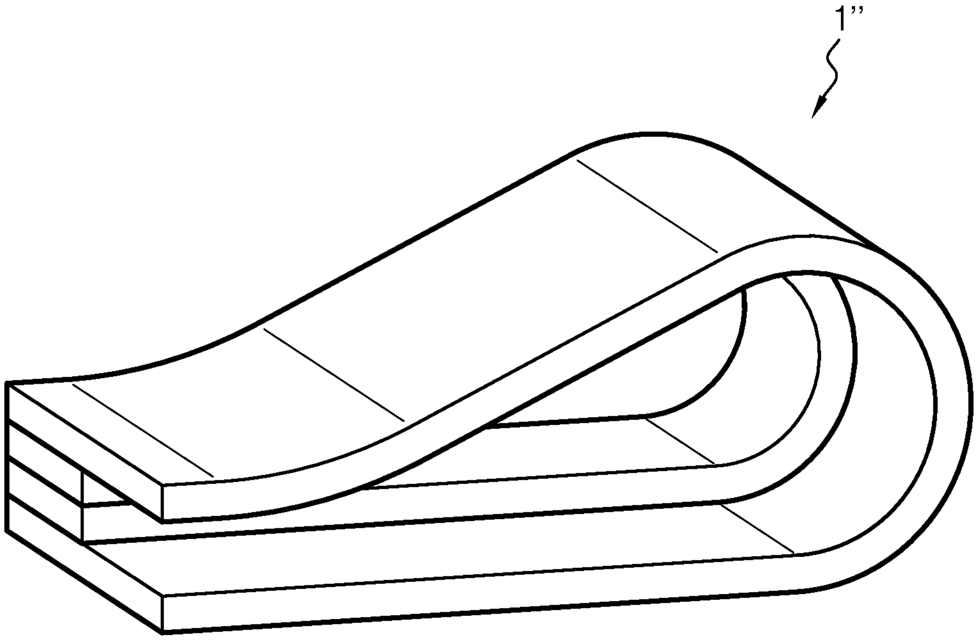
FIG. 11 is a perspective view of the device according to the third embodiment in a folded position.

A device 1" according to a third embodiment is shown in FIGS. 10-11.

Device 1" mainly differs from device 1' in that it does not comprises curved protrusion 24.

Device 1" can be regarded as a single flap which can be wound on itself in a folded, as shown in FIG. 11. Unlike the closed cavity defined by curved protrusion 24 and second flap 18, which is a globally tubular channel, the closed cavity defined by device 1" folded on itself has a teardrop profile.

Rib 40 may extend from first transversal edge 4 to a second transversal edge 6.

Like device 1', device 1" comprise a single shoulder 32.

Devices 1, 1' and 1" can be used for improving distribution of the adhesive composition and facilitates microsurgery, more preferably suture-less microsurgery. According to a specific embodiment, said microsurgery comprises repairing damaged biological tissue, and more particularly anastomosing damaged biological tissue. According to a specific embodiment, damaged biological tissue can be blood vessel, nerves, tendon, ligament and the like. According to the invention damaged biological tissue is cut or severed blood vessel, tendon, ligament or nerve. According to the invention, said microsurgery involves tubular structure which may be biological tissue, prosthetic material or combination thereof. According to a specific embodiment, prosthetic material can be a tube or conduit, for example a guide conduit such as conduits for helping to connect blood vessel or nerve tube or conduit for guiding nerve regeneration (for example nerve conduit, nerve wrap or shape-memory nerve conduit). According to another embodiment, the device 1 of the invention can be used for repairing damaged tubular biological structure (e.g. nerve, tendon, ligament or blood vessel), and more particularly for anastomosing two tubular biological structures (e.g. nerves, tendons, ligaments or blood vessels), using tubular prosthetic material.

The present invention further relates to a method using any of devices 1, 1' and 1" for repairing damaged tubular biological structure in a mammal.

According to one embodiment said damaged tubular biological structure is damaged blood vessel, damaged tendon, damaged ligament or damaged nerve.

The present invention further relates to a method using any of devices 1, 1' and 1" for connecting proximal and distal ends of tubular biological structure, more particularly transected tubular biological structure, in a mammal.

According to one embodiment said proximal and distal ends of tubular biological structure are proximal and distal ends of blood vessel. According to another embodiment said proximal and distal ends of tubular biological structure are proximal and distal ends of tendon or of ligament. According to another embodiment said proximal and distal ends of tubular biological structure are proximal and distal stumps of a transected nerve, more particularly transected peripheral nerve.

According to another embodiment said proximal and distal ends of tubular biological structure are proximal and distal stumps A and B of a transected nerve and the method further comprises the use of prosthetic material, more particularly of nerve conduit, nerve wrap or shape-memory nerve conduit 70 for nerve regeneration (FIG. 9). Nerve conduit 70 comprises a flexible sheet. The flexible sheet is made of a polymer able to wrap. Nerve conduit 70 is able to fit in channel 65 defined by body 2 in its folded position.

An embodiment of the method involving stumps A and B as well as device 1 is described with more details hereinafter. This method comprises the following steps. Proximal nerve stump A and a distal nerve stump B of transected nerve are positioned on nerve guide 70 laying flat on a support, such that ends of said stumps A, B face each other. Said support may for instance be body 2. In that case nerve guide 70 can lay flat on upper surface 22 defined by second flap 18.

Figure 12:
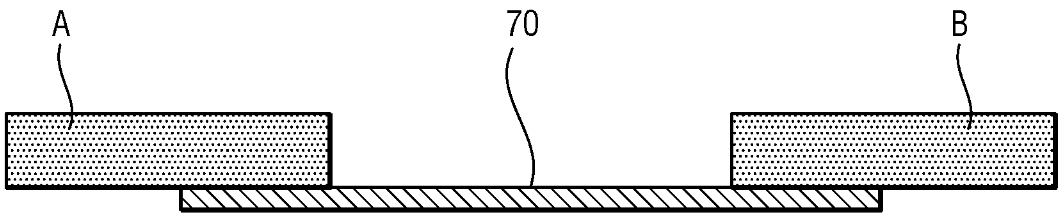
FIGS. 12-14, 16, 17 are cross-sectional view of elements involved in a method, at different stages of said method.

Nerve guide 70 is wrapped on itself around proximal stump A and distal stump B, so as to form a tube containing both ends facing each other. Both stumps A and B are separated by a nerve regeneration gap 71, as shown in FIG. 12. The distance between stump A and stump B may be less or equal to 5 millimeters. Alternatively, the nerve guide is a nerve conduit.

Figure 13:
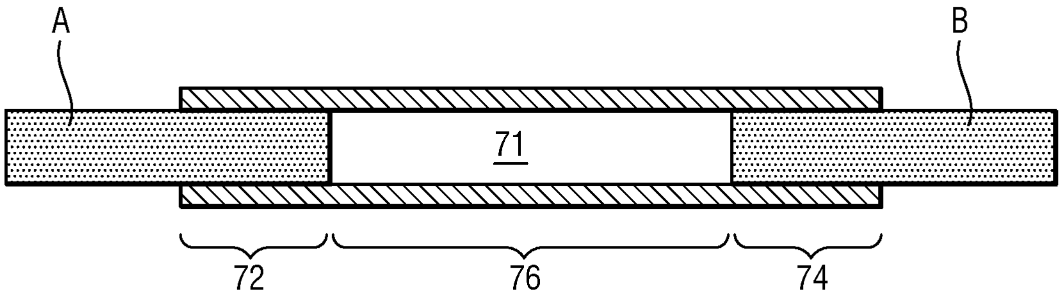

A first end portion 72 of nerve guide 70 surrounds and contacts proximal stump end A, as shown in FIG. 13. Similarly, a second end portion 74 of nerve guide 70 surrounds and contacts distal stump end B. Nerve guide 70 comprises a middle portion 76 connecting the first and second end portions 72, 74 of nerve guide 70 to each other. Middle portion 76 surrounds nerve regeneration gap 71. Nerve regeneration gap 71 corresponds to the prosthetic material section where nerve growth can occur leading to nerve regeneration and thus anastomosis.

If body 2 has not been used as support in preceding steps, unfolded body 2 is positioned under wrapped nerve guide 70 and both stump ends A, B, such that at least part of nerve guide 70 rests on upper surface 14.

Figure 14:
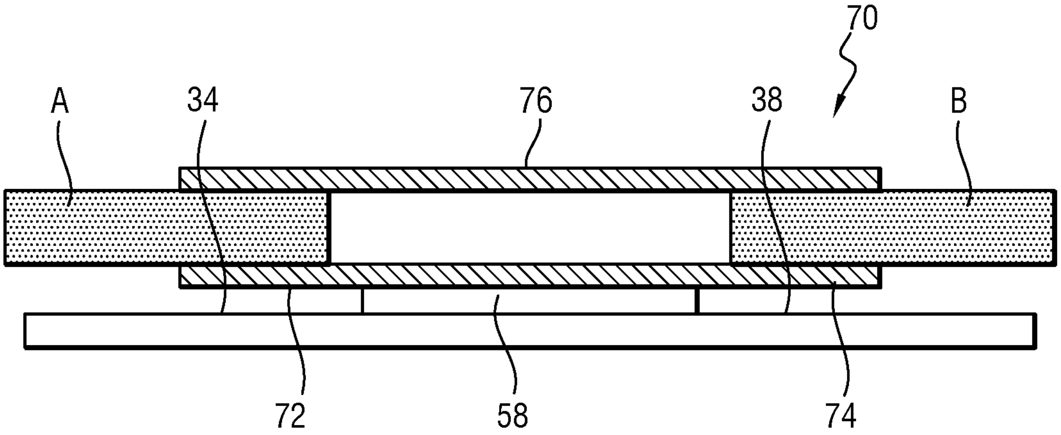
Figure 15:
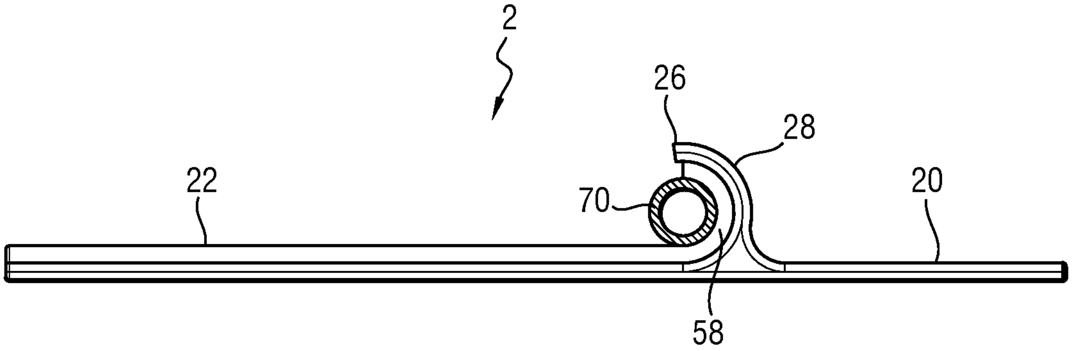
FIGS. 15, 18 are side views of the device of FIGS. 1-8 and a of prosthetic material.

As shown in FIGS. 14-15, nerve guide 70 is preferably positioned transversally in the open cavity defined by curved protrusion 24, such that the tube formed by nerve guide 70 is parallel to axis Y. Nerve guide 70 rests on concave rib portion 58. First end portion 72 of nerve guide 70 at least partially faces first recessed surface 34. However, first end portion 72 is separated from said first recessed surface 34 by the first recess due to first shoulder 32. Simultaneously, second end portion 74 at least partially faces second recessed surface 38. However, the second end portion 74 is separated from said second recessed surface 38 by the second recess due to second shoulder 36.

An adhesive composition is applied on both junction nerve guide 70/proximal stump end A and nerve guide 70/distal stump end B.

Figure 16:
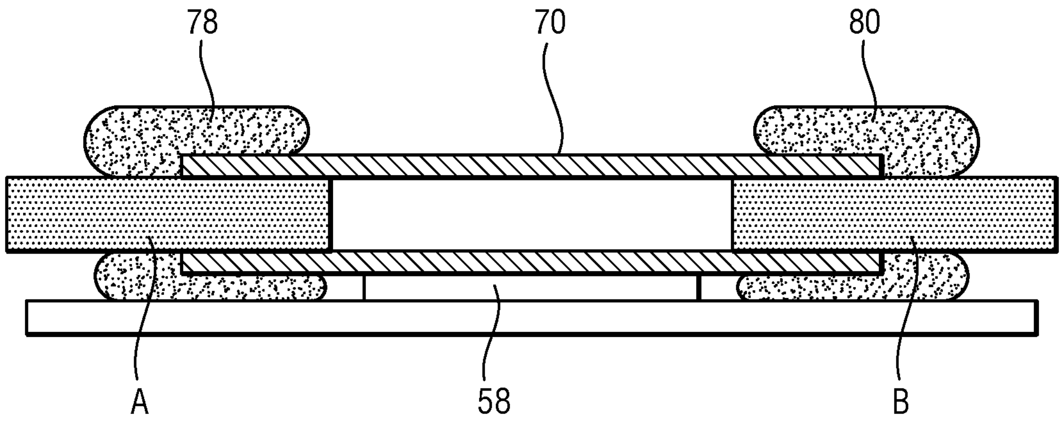

As shown in FIG. 16, a first layer 78 of said adhesive composition is applied so as to form a junction between nerve guide 70 (first end portion 72) and proximal stump end A. First layer 78 forms an annular junction between nerve guide 70 and proximal stump end A. It is to be noted that the first recess allows to apply said adhesive composition on the entire circumference of junction between proximal stump end A/first end portion 72 while nerve guide 70 rests on upper supper 14 of body 2.

Similarly, a second layer 80 of adhesive composition is applied so as to form a second junction between nerve guide 70 (second end portion 74) and distal stump end B. Second layer 80 forms an annular junction between nerve guide 70 and distal stump end B. It is to be noted that the second recess allows to apply said adhesive composition on the entire circumference of junction between distal stump B and second end portion 74 while nerve guide 70 rests on upper supper 14 of body 2.

Figure 17:
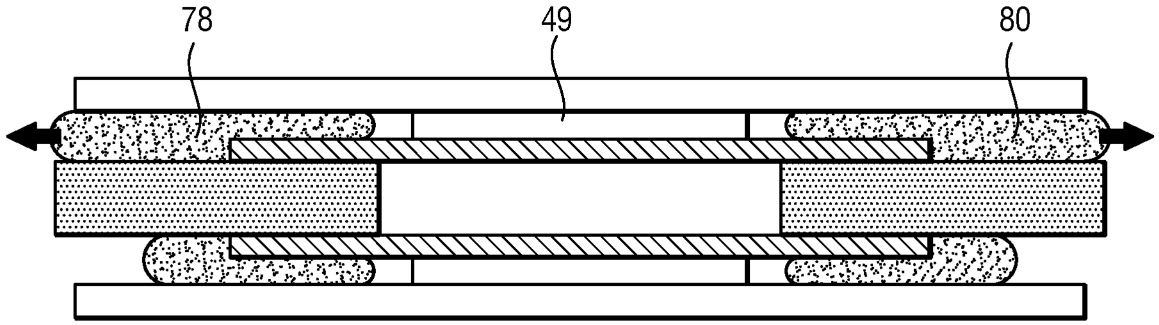
Figure 18:
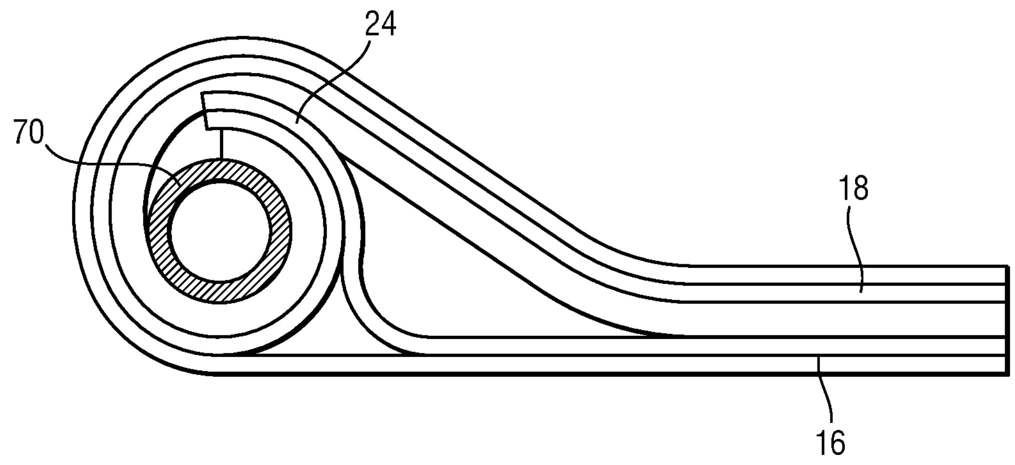

Flexible body 2 is positioned in the folded position by folding second flap 18 as described above so as to close the open cavity of curved protrusion 24 in which tubular nerve guide 70 is positioned, as shown in FIG. 18. During this step, second flap 18 can press on the first layer and/or on the second layer, thus causing any excess of applied adhesive to spurt out of body 2, as indicated by the black arrows depicted in FIG. 17.

Once flexible body 2 is in folded position (and maintained is said position by the maintaining means discussed above or manually), nerve guide 70 fits in channel 65 defined by curved protrusion 24 and second flap 18. The first recess defined by first shoulder 32 forms an annular gap separating first end portion 72 from first recessed surface 34. This annular shape of the first recess promotes a homogeneous distribution of the first adhesive layer 78 around junction between proximal stump end A/first end portion 72 of nerve guide 70. Similarly, the second recess defined by second shoulder 36 forms an annular gap separating second end portion 74 from second recessed surface 38. This annular shape of the second recess promotes a homogeneous distribution of the second adhesive layer 80 around junction between distal stump B and second end portion 74 of nerve guide 70.

Then layers 78, 80 are exposed to light so as to induce polymerization of said adhesive composition. As a consequence, both annular junctions formed by layers 78, 80 become rings maintaining proximal stump end A and distal stump end B in place in the nerve guide 70.

Then body 2 can be unfolded and moved away from stumps A, B and nerve guide 70.

The present disclosure is not limited to the embodiments shown in the figures. While the method has been disclosed in detail in FIGS. 9-15 for transected nerve, it must be understood that the device 1 can further be used when the damaged tubular biological structure is not fully transected, not transected but cut or partially damaged. Similarly, while device 1 according to the preferred embodiment comprises two shoulders and two recessed surfaces, it is possible to use device 1' or device 1" instead of device 1 (for example when tubular prosthetic structure is not used). According to a specific embodiment, any of devices 1, 1' and 1" can be used in microsurgery using suture (combination of suture and adhesive composition), for example for blood vessel anastomosis.

According to a preferred embodiment, the adhesive composition is able to polymerize when exposed to light. Before such polymerization the adhesive composition is fluid or viscous.

According to an embodiment of the invention, the adhesive composition comprises a pre-polymer comprising a polymeric unit of the general formula (-A-B-)n, wherein A represents a substituted or un-substituted ester, B represents a substituted or un substituted acid ester comprising at least two acid ester functionalities, and n represents an integer greater than 1.

Component A may be derived from a polyol, such as a diol, triol, tetraol or greater. Suitable polyols include diols, such as alkane diols; triols, such as glycerol, trimethylolpropane, triethanolamine; tetrads, such as erythritol, pentaerythritol; and higher polyols, such as sorbitol. Unsaturated diols, such as tetradeca-2,12-diene-1,14-diol, or other diols including macromonomer diols such as, for example polyethylene oxide, and N-methyldiethanoamine (MDEA) can also be used. Preferably, the polyol is substituted or unsubstituted glycerol.

Component B may be derived from a polyacid, such as a diacid or higher order acid. A wide variety of diacid, or higher order acids, can be used. Exemplary acids include, but are not limited to, citric acid (3 carbons), glutaric acid (5 carbons), adipic acid (6 carbons), pimelic acid (7 carbons), sebacic acid (8 carbons), and azelaic acid (nine carbons). Exemplary long chain diacids include diacids having more than 10, more than 15, more than 20, and more than 25 carbon atoms. Non-aliphatic diacids can also be used. For example, versions of the above diacids having one or more double bonds can be used to produce polyol-diacid copolymers. Preferably the diacid is substituted or unsubstituted sebacic acid.

Several substituents, such as amines, aldehydes, hydrazides, acrylates and aromatic groups, can be incorporated into the carbon chain. Exemplary aromatic diacids include terephthalic acid and carboxyphenoxy-propane. The polyacids, e.g. the diacids, can also include substituents as well. For example, reactive groups like amine and hydroxyl can be used to increase the number of sites available for cross-linking. Amino acids and other biomolecules can be used to modify the biological properties. Aromatic groups, aliphatic groups, and halogen atoms can be used to modify the inter chain interactions within the polymer.

The pre-polymer may further comprise a polyamide or polyurethane backbone. For example, polyamine (comprising two or more amino groups) may be used to react with polyacid together with polyol or after reacting with polyol. In other examples, polyisocianates (comprising two or more isocyanate groups) may be used to react with polyacid together with polyol or after reacting with polyol.

The pre-polymer is preferably able to be activated. It can be activated by introducing functional groups that can react or be reacted to form crosslinks. Suitable functional groups to be activated on the pre-polymer backbone include hydroxy groups, carboxylic acid groups, amines, and combinations thereof, preferably hydroxy and/or carboxylic acid. The free hydroxyl or carboxylic acid groups on the pre-polymer can be activated by functionalizing the hydroxy groups with a moiety which can form a crosslink between polymer chains. The groups that are activated can be free hydroxyl or carboxylic acid groups on A and/or B moieties in the pre-polymer. Preferably, the functional group is or contains an acrylate group. Acrylate groups are moieties containing substituted or unsubstituted acryloyl group. The acrylate may contain the following group: —C(=0)-CR1=CR2R3, wherein R1, R2, R3 are independently from one another, selected in the group consisting of H, alkyl such as methyl or ethyl, aryl such as phenyl, substituted alkyl, substituted aryl, carboxylic acid, ester, amide, amine, urethane, ether, and carbonyl. Preferably, R1, R2 and R3 are H; or R1 is CH3, R2 and R3 are H; or R1 and R2 are H and R3 is CH3; or R1 and R2 are H and R3 is phenyl. According to a preferred embodiment, the adhesive composition is a light-curable compound. "Light curable compound" refers to compounds that are configured to polymerize or otherwise cure upon receiving appropriate radiant energy, more particularly in the form of light from a light source.

Preferably, the light-curable compound comprises a pre-polymer and a photoinitiator, said photoinitiator being able to induce polymerization of the said pre-polymer when exposed to light of a specific wavelength.

According to a special embodiment, said photoinitiator is sensitive to ultraviolet (UV) radiations.

Examples of suitable photoinitiators sensitive to UV radiations include, but are not limited to: 2-dimethoxy-2-phenyl-acetophenone, 2-hydroxy-1-[4-(hydroxyethoxy)phenyl]-2-methyl-1-propanone (Irgacure 2959), 1-hydroxycyclohexyl-1-phenyl ketone (Irgacure 184), 2-hydroxy-2-methyl-1-phenyl-1-propanone (Darocur 1 173), 2-benzyl-2-(dimehylamino)-1-[4-morpholinyl) phenyl]-1-butanone (Irgacure 369), methylbenzoylformate (Darocur MBF), oxy-phenyl-acetic acid-2-[2-oxo-2-phenyl-acetoxy-ethoxy]-ethyl ester (Irgacure 754), 2-methyl-1-[4-(methylthio)phenyl]-2-(4-morpholinyl)-1-propanone (Irgacure 907), diphenyl(2,4,6-trimethylbenzoyl)-phosphine oxide (Darocur TPO), phosphine oxide, phenyl bis(2,4,6-trimethyl benzoyl) (Irgacure 819), and combinations thereof. According to another embodiment, said photoinitiator is sensitive to visible light (typically blue light or green light).

Examples of photoinitiators sensitive to visible light include, but are not limited to: diphenyl(2,4,6-trimethylbenzoyl)-phosphine oxide, eosin Y disodium salt, N-Vinyl-2-Pyrrolidone (NVP) and triethanolamine, and camphorquinone.

In addition, the adhesive composition may also contain one or more pharmaceutical, therapeutic, prophylactic agents that can be released during the time period that the material functions as an adhesive. The agent may be a small molecule agent, for example having molecular weight less than 2000, 1500, 1000, 750, or 500 Da, a biomolecule, for example peptide, protein, enzyme, nucleic acid, polysaccharide, growth factors, cell adhesion sequences such as RGD sequences or integrins, extracellular matrix components, or combinations thereof. Similarly, the adhesive composition may also contain cells or biological tissue or particulate bone grafts or/and bone substitutes. Exemplary classes of small molecule agents include, but are not limited to, anti-inflammatories, analgesics, antimicrobial agents, and combinations thereof. Exemplary extracellular matrix components include, but are not limited to, collagen, fibronectin, laminin, elastin and combinations thereof.

Preferably, the adhesive composition is or comprises poly glycerol sebacate acrylate (PGSA).

The invention claimed is:

1. A device for applying adhesive composition to biological tissue or prosthetic material, the device comprising a flexible body, wherein:
   - the body has a first longitudinal edge, a second longitudinal edge and an upper surface comprising a first shoulder defining a first recess,
   - the body is adapted to be folded on itself in a folded position in which the body defines a channel and said first recess is configured to form an annular gap between the upper surface and the biological tissue or prosthetic material when the biological tissue and/or prosthetic material is positioned in the channel,
   - the first recess extends along the first longitudinal edge of the body, and
   - the body further comprises a curved protrusion defining a concave portion of the upper surface.

2. The device according to claim 1, wherein the first recess has a depth from 0.1 millimeters to 10 millimeters.

3. The device according to claim 1, wherein the first shoulder extends in the curved protrusion.

4. The device according to claim 1, wherein the curved protrusion has a radius of curvature from 1 millimeter to 15 millimeters.

5. The device according to claim 1, wherein the curved protrusion has a radius of curvature from 1 millimeter to 10 millimeters.

6. The device according to claim 1, wherein the curved protrusion has a radius of curvature from 1 millimeter to 5 millimeters.

7. The device according to claim 1, wherein the curved protrusion extends over an angular sector of at least 90 degrees.

8. The device according to claim 1, further comprising a deformable flap defining a deformable portion of the body and further defining a first end of the body, wherein the channel is defined by the curved protrusion and the deformable flap.

9. The device according to claim 8, further comprising a prehensile flap defining a second end of the body which is opposite to the first end, and wherein the curved protrusion connects the prehensile flap to the deformable flap.

10. The device according to claim 1, wherein:
   - the upper surface of the body comprises a second shoulder defining a second recess spaced from the first recess,
   - the second recess extends along the second longitudinal edge of the body,
   - the body is adapted to be folded on itself into the folded position in which the body defines the channel and said first recess is configured to form a first annular gap and said second recess is configured to form a second annular gap, wherein the first annular gap and the second annular gap are formed between the upper surface of the body and the biological tissue or prosthetic material when the biological tissue or prosthetic material is positioned in the channel.

11. The device according to claim 10, wherein the body comprises a rib separating the second recess from the first recess, said first and second shoulders extending along respective lengthwise edges of the rib.

12. The device according to claim 1, wherein the first recess has a width from 1 millimeter to 10 millimeters.

13. The device according to claim 1, wherein the body is translucent or comprises silicone.

14. A kit comprising a device according to claim 1 and an adhesive composition.

15. The kit according to claim 14, wherein the adhesive composition is capable of being polymerized when exposed to light.

16. The kit according to claim 14, further comprising a scaffold for tissue regeneration.

17. A method comprising repairing damaged tubular biological structure in a mammal using the kit according to claim 14.

18. A method comprising repairing damaged tubular biological structure in a mammal using the device according to claim 1.

* * * * *